United States Patent [19]

Politi et al.

[11] Patent Number: 5,091,172
[45] Date of Patent: Feb. 25, 1992

[54] COSMETIC USE OF 3-INDOLEPYRUVIC ACID

[75] Inventors: Vincenzo Politi; Giovanna De Luca; Giovanni Di Stazio; Mario Materazzi, all of Rome, Italy

[73] Assignee: Polifarma S.p.A., Rome, Italy

[21] Appl. No.: 562,842

[22] Filed: Aug. 6, 1990

[30] Foreign Application Priority Data

Aug. 8, 1989 [IT] Italy ................. 48285 A/89

[51] Int. Cl.$^5$ .................. A61K 7/40; A61K 7/42; A61K 7/48
[52] U.S. Cl. .................... 424/59; 514/844; 514/847

[58] Field of Search ........................... 424/59

[56] References Cited

U.S. PATENT DOCUMENTS 4,551,471  11/1985  De Luca et al. .......... 514/419
4,808,728   2/1989  De Luca et al. .......... 548/502

Primary Examiner—Dale R. Ore
Attorney, Agent, or Firm—Birch, Stewart, Kolasch & Birch

[57] ABSTRACT

A description is given of the cosmetic use of 3-indolepyruvic acid for the protection of the skin from damage caused by oxygen, by the sun and by aging.

3 Claims, No Drawings

5,091,172

COSMETIC USE OF 3-INDOLEPYRUVIC ACID

BACKGROUND OF THE INVENTION

1. Field of the Invention

The present invention relates to the cosmetic use of 3-indolepyruvic acid for the protection of the skin against damage caused by oxygen, by the sun and by aging.

In the present society the use of cosmetic products, intended as locally applied preparations for the cleaning, protection, deodorization, perfuming and decoration of the surface of the epidermis, without having any therapeutic effects, has become more and more common. Among the many locally applied preparations great importance has been assumed, especially in recent years, by those products whose object is to protect the skin from damage caused by oxygen, by the sun and by the aging process.

2. Description of the Prior Art

It has been known for several years that oxygen free radicals, when produced by the organism in quantities greater than the capacity for disintoxication with which all living beings are provided, can easily attack the basic cell structures, such as nucleic acids, proteins and membranes, bringing about in the end the death of the cells of, and thus inducing degenerative diseases in all the types of tissue which are attacked. This attack is particularly dangerous in the case of disease of the skin cells.

In a volume published by Raven Press in 1984 ("Free radicals in Molecular Biology, Aging and Disease"), the excessive presence of oxygen free radicals was considered to be the cause not only of the above mentioned diseases, but also of the normal aging to which all living beings are subject.

3-indolpyruvic acid is a known compound per se: its production is cited for example in the U.S. Pat. No. 4551471, in which a process for its enzymatic synthesis is described using the enzyme aspartate amminotransferase, and in the published international application No. WO87/00169, in which a process for the chemical synthesis of said 3 indolepyruvic acid is described using a coupling reaction starting from 1-tryptophan.

Also belonging to the state of the art is the use of 3-indolepyruvic acid for the treatment of diseases of the central nervous system caused by an excess of excitatory amino acids as described in International patent application No. WO88/09789.

It has now been surprisingly found that 3-indolpyruvic acid is a powerful inhibitor of the effects of oxygen free radicals, of exposure to ultra-violet rays and the relative aging of the skin.

SUMMARY OF THE INVENTION

Object of the present invention is therefore an active cosmetic agent formed by 3-indolepyruvic acid for the protection of the skin from damage caused by oxygen, by the sun and by aging.

The use of indolepyruvic acid in the cosmetic field is not known from the prior art.

The effect of 3-indolpyruvic acid in counteracting the free radical effects will be hereinafter described on the basis of experimental tests.

Evaluation of the antiradical activity of 3-indolepyruvic acid (IPA)

In order to evaluate the production of oxygen free radicals in tissues or in biological fluids, the method most commonly used is that of the production of malondialdehyde (MDA), as described for example in Methods in Enzymology vol. 105, 1984.

In brief, said method is based on the fact that the unsaturated fatty acids, basic constituents of biological membranes, are attacked by oxygen free radicals, which break the carbon chain in a number of places, until giving MDA as a final product. The aldehyde is then detected using a simple colorimetric method. A test was therefor carried out to evaluate the formation of MDA in the presence of, and in the absence of, IPA.

Evaluation of the radicalic activity in "in vitro" systems

This test has the object of evidencing a direct intervention of IPA (thus excluding the intervention of other metabolites which can be formed from IPA in biological fluids) in the capture of free radicals present in the solution.

The production of radicals was activated by means of a system comprising iron ion, ascorbate and phosphatidylcholine (the most common constituent of biological membranes).

| IPA dose | % MDA inhibition |
|---|---|
| $5 \times 10^{-6} M$ | 10 |
| $1 \times 10^{-5} M$ | 35 |
| $2 \times 10^{-5} m$ | 65 |

The results show that IPA is capable of blocking "in vitro" the degenerating effects of oxygen on the unsaturated fatty acids present in biological membranes. Furthermore the results show that the effect is dose-dependent.

From the foregoing it can be concluded that IPA has demonstrated its capacity to powerfully antagonize the radicalic chain reactions which are activated by oxygen free radicals on biological membranes.

As to efficiency, IPA compares favourably with the best known oxidizing agents.

The tests on capture of free radicals have been extended with the object of evaluating whether the phenomenon can be generalized, or whether it is restricted to an intervention on biological tissues.

Evaluation of the antiradical activity of IPA using DPPH test

The compound DPPH (diphenyl-picryl-hydrazyl) is a stabilized free radical, which remains unaltered in ethanol for relatively long periods of time. The compounds which act as "radical scavengers" can be evaluated by following the decrease of optical density on the spectophotometer (517 nm) after addition to the solution containing DPPH. IPA has shown itself to be an excellent free radical scavenger, as a notable decrease of optical density (40% over 30 minutes) can be seen when the compound is added at the dose of $10^{-6}M$.

Evaluation of the antiradical activity of IPA using the chemiluminescence method Chemiluminescence is a means of analysis which in recent years has gained more and more importance for the determination of various compounds having a short life. It appears to be particularly advantageous for the determination of oxygen free radicals, as these produce a basic chemiluminescence which can be enhanced with luminol (see for example Biochem. Biophys. Res. Communic. 150, 39-44, 1988). With this technique it is very easy to evaluate the antiradical effect of a compound, thanks to the decreased emission of light registered on special instruments (luminographs).

Using as a source of free radicals the system $Fe^{++}$/hydrogen peroxide, IPA has been shown to inhibit the chemiluminescence emitted by luminol by the following percentage:

| IPA concentration | % inhibition |
|---|---|
| $2.5 \times 10^{-8}$ M | 0 |
| $1 \times 10^{-7}$ M | 70 |
| $2.5 \times 10^{-6}$ M | 100 |

The above results indicate that the antiradical effect of IPA becomes even stronger when there are no phospholipids present in the solution. Furthermore, it is confirmed that this compound has a reactivity comparable to that of the most widely used antioxidants known to date (see Biochem. Biophys. cited above).

Antimutagenic effect of IPA

As oxygen free radicals are often suspected of being the initial cause of the mutagenic activity of numerous chemical compounds which are dangerous for man and, as IPA has shown itself to be an extremely good free radical inhibitor, experiments were carried out to evaluate an antimutagenic effect of IPA.

To do this, the strain TA 100 of Salmonella Typhimurium was used, set in culture on a plate in a histidine-free medium. As it is well known from the state of the art, in this situation the bacteria cannot grow and reproduce normally, but only those individuals will reproduce which, having undergone a casual mutation in their genetic makeup, are able to adapt to the absence of histidine. In a normal situation, between 100 and 200 colonies per plate can be counted, which represent the number of individuals with spontaneous mutation. When a mutagenic agent is added to the culture medium, it induces a greater series of mutations in the bacteria, so that the number of salmonella colonies becomes much larger, with an increase proportional to the strength of the mutagen.

As known mutagenic agents the following were used: 4-nitroquinoline-N-oxide (4NQO), 2-nitrofluorene (2NF), Captan and Folpet. The results obtained by incubating the salmonella with mutagenic agents in the presence or in the absence of IPA (1 mg/plate) are shown in the following table.

| AGENT | (number of salmonella colonies/plate) | | |
|---|---|---|---|
| | DOSE/PLATE | MUTAGEN ALONE | + IPA |
| 4NQO | 0.035 mcg | 380 | 180 |
| 4NQO | 0.070 mcg | 590 | 200 |
| 4NQO | 0.125 mcg | 950 | 210 |
| 4NQO | 0.250 mcg | 1500 | 260 |
| 2NF | 1 mcg | 280 | 200 |
| 2NF | 2 mcg | 400 | 210 |
| 2NF | 4 mcg | 650 | 240 |
| 2NF | 8 mcg | 1150 | 260 |
| Captan | 1.25 mcg | 350 | 180 |
| Captan | 2.50 mcg | 500 | 200 |
| Captan | 5.00 mcg | 850 | 220 |
| Captan | 10 mcg | 1200 | 240 |
| Captan | 20 mcg | 1600 | 320 |
| Folpet | 12.5 mcg | 400 | 180 |
| Folpet | 25 mcg | 700 | 200 |
| Folpet | 50 mcg | 950 | 240 |
| Folpet | 100 mcg | 1300 | 320 |

The results obtained in these tests indicate that IPA is capable of effectively countering the mutagenic effect of notoriously dangerous compounds. As the reduction of the number of colonies formed is quite considerable, and in practice, in the presence of IPA the number of colonies formed does not differ much from the number which are formed by spontaneous mutation it can be concluded that IPA is a powerful antimutagenic agent.

Summarizing the results obtained IPA (3-indolpyruvic acid) has been shown to have a powerful antagonizing effect on free radicals originating from oxygen which are responsable for the aging of the skin.

The results obtained therefore confirm the possibility of the use of 3-indolepyruvic acid as a cosmetic agent for the protection of the skin from the effect of oxygen and of exposure to the sun radiation, for the maintenance of elasticity in the skin itself, counteracting the aging caused by free radicals.

A further object of the present invention is a composition for cosmetic use containing 3-indolepyruvic acid and one or more compatible vehicle or excipient for the protection of the skin from the damage caused by oxygen, by exposure to the sun and by aging caused by free radicals. The preferred proportion for use in said composition of 3-indolepyruvic acid are between 0.5 and 20% by weight, to the weight of the entire composition, a particularly preferred proportion being from 5 to 15% by weight.

As excipients and additives to be used in the composition for cosmetic use according to the present invention, all those well known to the state of the art can be cited, dependent upon the type of formulation such as creme, lotion, paste, pomade, and the like, according to the method of application.

We claim:

1. A method for the protection of the skin from damage caused by oxygen, by exposure to the sun and by aging, comprising applying to the skin an amount sufficient to protect the skin, of 3-indolepyruvic acid.

2. The method according to claim 1 wherein the 3-indolepyruvic acid is incorporated in an amount of 0.5-20% by weight in a composition, the remaining being a compatible vehicle or excipient.

3. The method according to claim 2 wherein the 3-indolepyruvic acid is incorporated in an amount of from 5 to 15% by weight.

* * * * *